US008957252B2

(12) United States Patent
Rajadhyaksha et al.

(10) Patent No.: US 8,957,252 B2
(45) Date of Patent: Feb. 17, 2015

(54) PROCESS FOR PREPARATION OF LACOSAMIDE AND SOME N-BENZYL-PROPANAMIDE INTERMEDIATE DERIVATIVES

(75) Inventors: Mangesh Narayan Rajadhyaksha, Mumbai (IN); Ranjeet Nair, Mumbai (IN); Nilesh Balkrishna Shrigadi, Mumbai (IN); Aditi Milind Panandikar, Mumbai (IN)

(73) Assignee: Indoco Remedies Limited, Mumbai (IN)

( * ) Notice: Subject to any disclaimer, the term of this patent is extended or adjusted under 35 U.S.C. 154(b) by 214 days.

(21) Appl. No.: 13/811,707

(22) PCT Filed: Jul. 26, 2011

(86) PCT No.: PCT/IN2011/000494
§ 371 (c)(1),
(2), (4) Date: Jan. 23, 2013

(87) PCT Pub. No.: WO2012/014226
PCT Pub. Date: Feb. 2, 2012

(65) Prior Publication Data
US 2013/0123522 A1 May 16, 2013

(30) Foreign Application Priority Data
Jul. 27, 2010 (IN) .......................... 2136/MUM/2010

(51) Int. Cl.
C07C 233/16 (2006.01)
C07C 237/06 (2006.01)
C07C 247/06 (2006.01)
C07C 231/14 (2006.01)
C07C 231/02 (2006.01)
C07C 231/12 (2006.01)
C07C 247/12 (2006.01)
C07C 269/04 (2006.01)
C07C 235/06 (2006.01)
C07C 247/04 (2006.01)

(52) U.S. Cl.
CPC ............. *C07C 231/14* (2013.01); *C07C 231/02* (2013.01); *C07C 231/12* (2013.01); *C07C 247/12* (2013.01); *C07C 269/04* (2013.01); *C07C 235/06* (2013.01); *C07C 247/04* (2013.01)
USPC .............................. 564/158; 564/194; 552/12

(58) Field of Classification Search
USPC ..................... 552/12; 564/158, 194
See application file for complete search history.

(56) References Cited

U.S. PATENT DOCUMENTS

| 5,773,475 A | 6/1998 | Kohn |
| 2008/0027137 A1 | 1/2008 | Riedner et al. |
| 2009/0143472 A1 | 6/2009 | Madhra et al. |

FOREIGN PATENT DOCUMENTS

| EP | 1344763 A | 9/2003 |
| GB | 836332 A | 6/1960 |
| WO | 2010052011 A | 5/2010 |

OTHER PUBLICATIONS

Raghavan et al., The sulfinyl moiety as an internal nucleophile, Part 8: Efficient, stereospecific synthesis of (+)—polyoxamic acid. Tetrahedron Letters, vol. 44, No. 35, 25 Aug. 2003, pp. 6713-6715.
Effenberger et al., Amindo Acids; 13 Investigations on the Synthesis of DL-Serine From Alpha-Haloacrylic Acid Derivatives. Tetrahedron, vol. 44, No. 17, Jan. 1, 1988, pp. 5573-5582.
Kumiko Takeuchi et al., Development of Dual-Acting Agents for Thromboxane Receptor Antagonism and Thromboxane Synthase Inhibition. 3. Synthesis and Biological Activities of Oxazolecarboxamide-Substituted [omega]-Phenyl-[omega]-(3-pyridyl)alkenoic Acid Derivatives and Related Compounds. Journal of Medicinal Chemistry, vol. 41, No. 27, Dec. 1, 1998, pp. 5362-5374.
Morieux et al., Synthesis and anticonvulsant activities of N-benzyl (2R)-2-acetamido-3-oxysubstituted propionamide derivatives. Bioorganic & Medicinal Chemistry. vol. 16, Issue 19, Oct. 1, 2008, pp. 8968-8975.
Anderson et al., Reinvestigation of the mixed carbonic anhydride method of peptide synthesis. J. Am. Chem. Soc., 1967, 89 (19), pp. 5012-5017 (Abstract).
Petit et al., Ethyl Gycidate from (s)-Serine: Ethyl (R)-(+)-2-3-Epoxypropanoate. Organic Syntheses, Coll. vol. 10, p. 401 (2004); vol. 75, p. 37 (1998).
International Search Report dated Dec. 21, 2011 for PCT/IN2011/000494.

*Primary Examiner* — Barbara P Badio
(74) *Attorney, Agent, or Firm* — Kramer Amado, P.C.

(57) ABSTRACT

The present invention discloses novel process for the preparation of (2R)-2-acetamido-N- benzyl-3-methoxypropanamide of Formula I involving novel intermediates of Formula-XIX and Formula-XX.

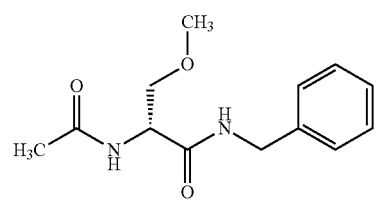

Formula I

21 Claims, No Drawings

PROCESS FOR PREPARATION OF LACOSAMIDE AND SOME N-BENZYL-PROPANAMIDE INTERMEDIATE DERIVATIVES

FIELD OF THE INVENTION

The present invention relates to preparation of novel intermediate and novel process for the preparation of (2R)-2-acetamido-N-benzyl-3-methoxypropanamide.

BACKGROUND AND PRIOR ART

The compound (2R)-2-acetamido-N-benzyl-3-methoxypropanamide of Formula-I having an international non-proprietary name Lacosamide is an anticonvulsant drug for the treatment of central nervous system disorder such as epilepsy. It is also useful in the treatment of pain particularly diabetic neuropathic pain.

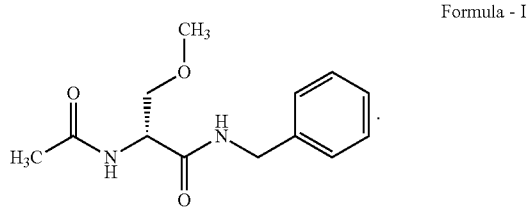 [SMILES: COC[C@@H](NC(C)=O)C(=O)NCc1ccccc1]

Formula - I

U.S. Pat. No. 5,773,475 for first time reported the preparation of Lacosamide of Formula-I by three different methods. In the first method, D-serine is esterified followed by treating the D-serine methyl ester with benzylamine to result the compound (2R)-2-amino-N-benzyl-3-hydroxypropanamide of Formula-II. The compound of Formula-II is acetylated with acetic anhydride in solvent dichloromethane to give the compound (2R)-2-acetamido-N-benzyl-3-hydroxypropanamide of Formula-III. The compound of Formula-III is methylated using methyl iodide in the presence of silver oxide and solvent acetonitrile to give Lacosamide of Formula-I.

The second method describes the process, wherein D-serine is protected with benzyloxycarbonyl chloride to give N-Benzyloxycarbonyl-D-serine of Formula-IV. The compound of Formula-IV on alkylation with methyl iodide in the presence of silver oxide and solvent acetonitrile yields the compound (2R)-methyl 2-(benzyloxycarbonylamino)-3-methoxypropanoate of Formula-V, and which is purified by flash column chromatography using silica gel and methanol-chloroform eluent before the next stage. The compound of Formula-V is hydrolyzed to give (2R)-2-(benzyloxycarbonylamino)-3-methoxypropanoic acid of Formula-VI. The compound of Formula-VI is cooled to −78° C. in tetrahydrofuran and reacted with isobutyl chloroformate in presence of N-methylmorpholine followed by reaction with benzylamine to yield the compound (2R)-benzyl 1-(benzylamino)-3-methoxy-1-oxopropan-2-ylcarbamate of Formula-VII. The compound of Formula-VII on hydrogenation using palladium on carbon gives deprotected compound (2R)-2-amino-N-benzyl-3-methoxy-propanamide of Formula-VIII. The compound of Formula-VIII is acetylated using acetic anhydride in the presence of solvent pyridine to give crude Lacosamide of the Formula-I. The crude compound is purified by flash column chromatography to give pure Lacosamide.

The third method described in the patent, wherein D-serine is first acetylated to give N-acetylserine, which is taken in tetrahydrofuran and cooled to −78° C. to react with isobutyl chloroformate in the presence of N-methylmorpholine followed by reaction with benzylamine to give (2R)-2-acetamido-N-benzyl-3-hydroxypropanamide of Formula-III. The compound of Formula-III is purified by flash column chromatography and taken for alkylation with methyl iodide in the presence of silver oxide and solvent acetonitrile to give Lacosamide of Formula I. The reaction sequence of above three methods can be represented in Scheme-1.

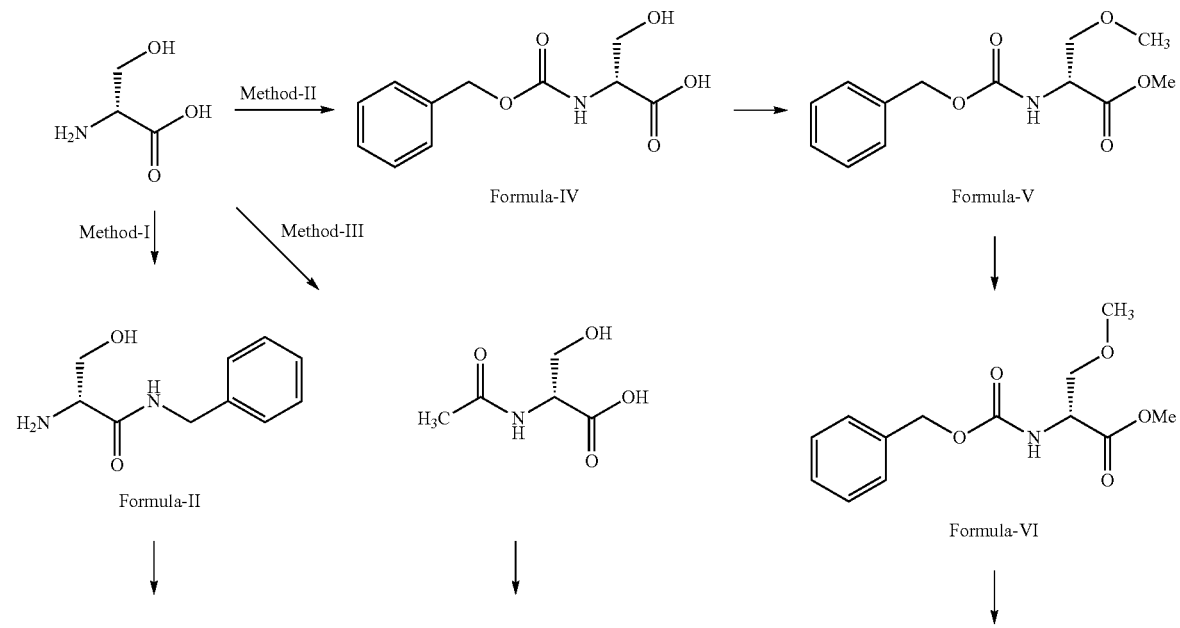

Scheme-1

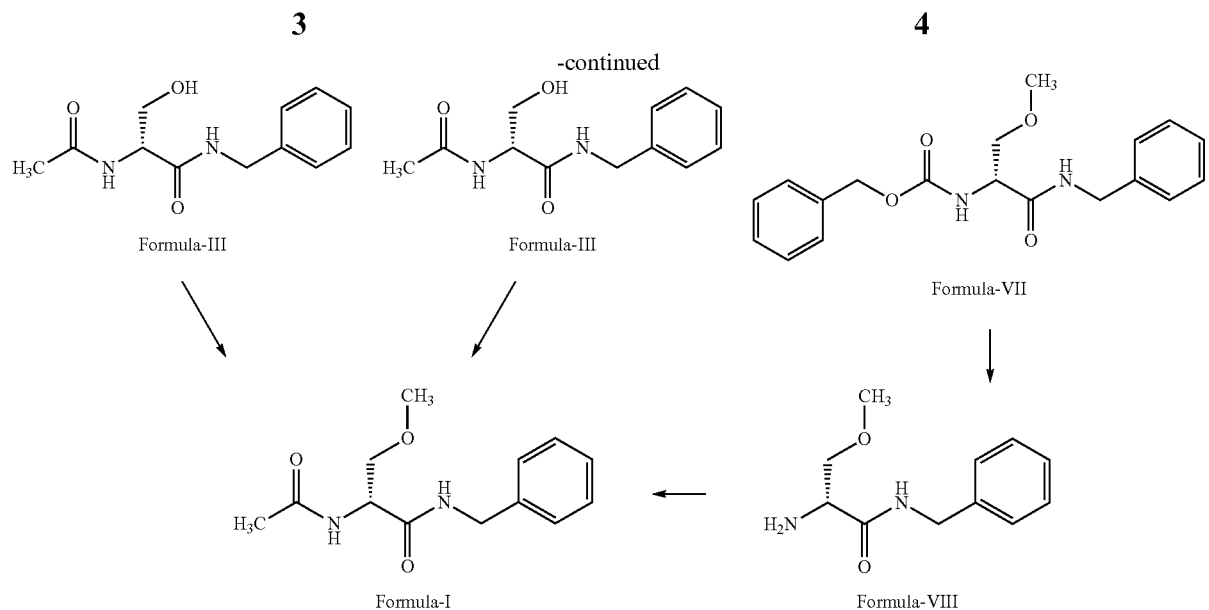

Another patent application U.S.2009143472, discloses the process for preparation of Lacosamide of Formula-I, wherein D-serine is treated with trimethylsilyl chloride to protect the hydroxyl group and then reacted with trityl chloride followed by deprotection of hydroxyl group to isolate the protected compound N-trityl-D-serine of Formula-IX. The compound of Formula-IX is alkylated with methyl iodide in the presence of sodium hydride and imidazole at −15 to −5° C. to get the compound O-methyl-N-trityl-D-serine of Formula-X. The compound of Formula-X is reacted with isobutyl chloroformate in presence of N-methylmorpholine and followed by reaction with benzylamine to get the compound (2R)-N-benzyl-3-methoxy-2-(tritylamino)propanamide of Formula-XI. The compound of Formula-XI on deprotection yields the compound (2R)-2-amino-N-benzyl-3-methoxypropanamide of Formula-VIII, which on acetylation with acetic anhydride in the presence of dimethylaminopyridine yields Lacosamide of Formula-I. The reaction sequence is as given in Scheme-2;

Another U.S. patent application U.S.2008027137 describes the preparation of Lacosamide of Formula-I, wherein N-protected D-serine is O-methylated with either using dimethyl sulfate in presence of phase-transfer catalyst and sodium hydroxide or with butyllithium and dimethyl sulfate to get the compound (2R)-2-(tert-butoxycarbonylamino)-3-methoxypropanoic acid of Formula-XII. The compound of Formula-XII is reacted with benzylamine as per the process disclosed earlier to get the compound (2R)-tert-butyl 1-(benzylamino)-3-methoxy-1-oxopropan-2-ylcarbamate of Formula-XIII. Deprotection of the compound of Formula-XIII with hydrochloric acid yields the compound (2R)-2-amino-N-benzyl-3-methoxy-propanamide of Formula-VIII, which on acetylation yields the compound Lacosamide of Formula-I. The reaction sequence is as given in Scheme-3.

Scheme-2

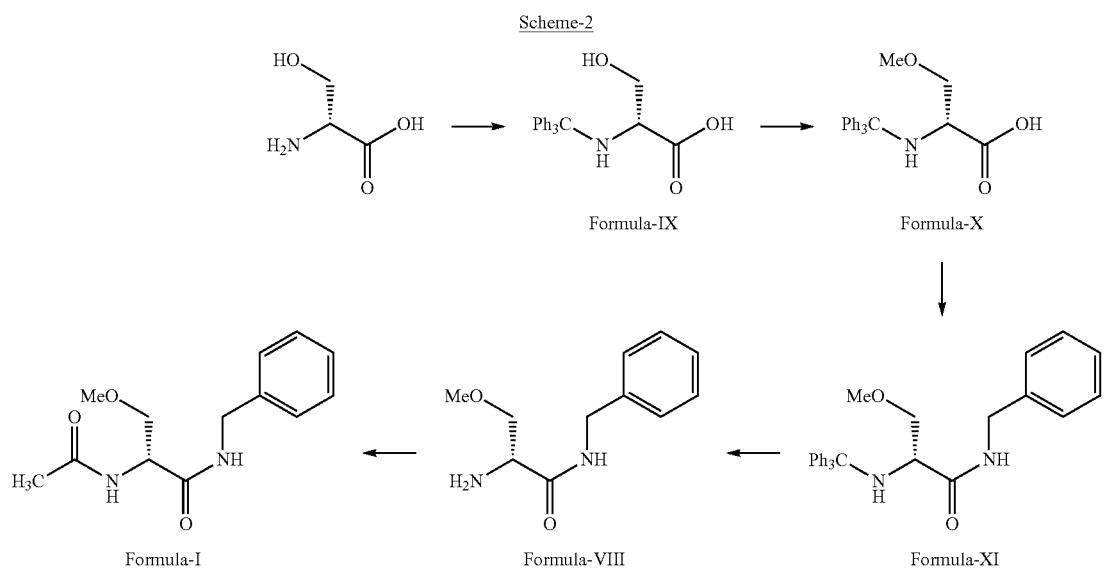

Scheme-3

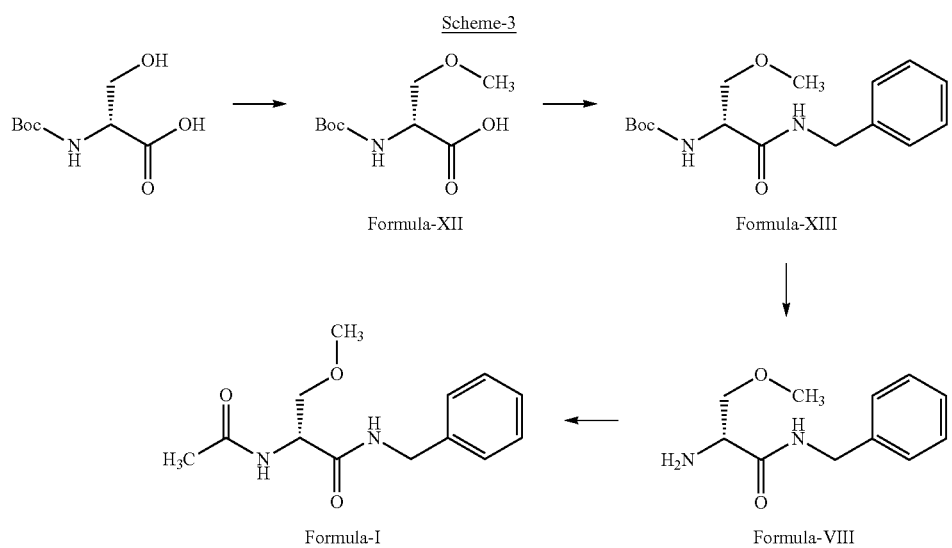

Another method for the preparation of Lacosamide of Formula-I was described in the Journal Bioorganic & Medicinal Chemistry, 16(19), 8968-8975 (2008), wherein D-serine methyl ester is treated with diethoxytriphenylphosphorane to give 9:1 mixture of (R)-aziridine-2-carboxylic acid methyl and ethyl ester of Formula-XIV. The mixture of compound of Formula-XIV on acetylation with acetic anhydride in the presence of triethylamine and dimethylaminopyridine gives a mixture of (R)-1-acetylaziridine-2-carboxylic acid methyl and ethyl ester of Formula-XV. The mixture of compound of Formula-XV is treated with methanol in the presence of borontrifluoride etherate $BF_3.Et_2O$ to give a mixture of (2R)-2-acetamido-3-methoxypropanic acid methyl and ethyl ester of Formula-XVI. The compound of Formula-XVI on hydrolysis with lithium hydroxide yields the compound (2R)-2-acetamido-3-methoxypropanoic acid of Formula- XVII; which on reaction with benzylamine in presence of tetrahydrofuran and 4-(4,6-dimethoxy-1,3,5-triazin-2-yl)-4-methylmorpholinium chloride followed by purification of the product using flash column chromatography (10:90 MeOH/$CHCl_3$) yields compound Lacosamide of Formula-I. The reaction sequence is as given in Scheme-4;

Scheme-4

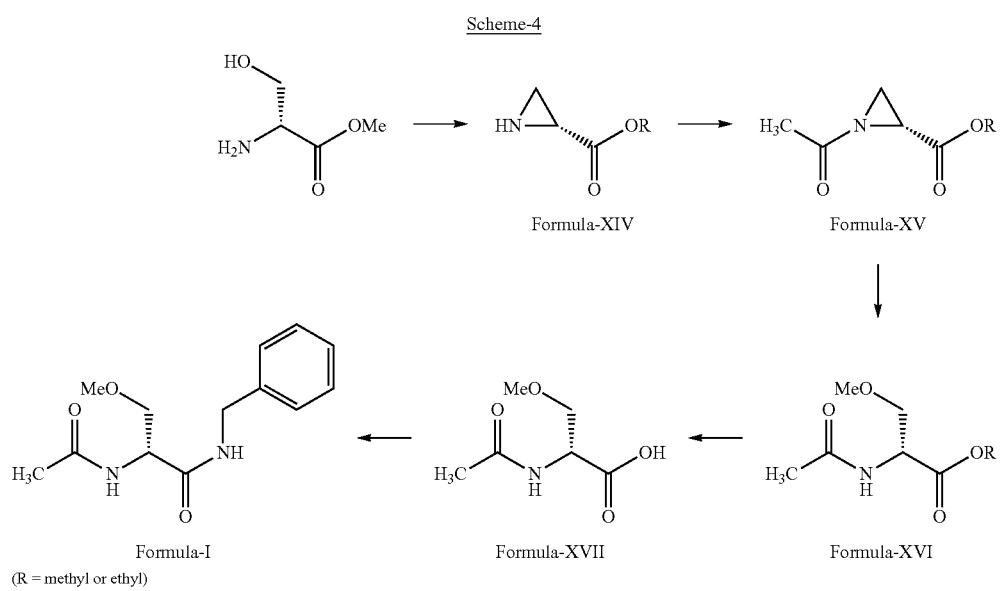

(R = methyl or ethyl)

The drawbacks of the above described processes are:

i. Use of expensive D-serine or its derivatives as starting material;

ii. O-methylation involves the use of methyl iodide and silver oxide, which is expensive;

iii. Lower temperature required to carry out the amide formation reaction;

iv. The purification using flash column chromatography to purify the intermediates and the final compounds renders the process industrially unviable.

It is therefore required to develop an alternative and improved process for the preparation of Lacosamide which overcomes the problems associated with the processes known in the art.

The present inventors ameliorates the problems of the prior art processes by using cost effective, naturally occurring starting material and avoiding the use of Flash column chromatography for the purification of product Lacosamide of Formula-I.

OBJECTIVES OF THE INVENTION

The main objective of the present invention is to prepare highly pure compound (2R)-2-acetamido-N-benzyl-3-methoxypropanamide of Formula-I with an industrially useful cost effective process.

Another objective of the present invention is to prepare novel intermediate compound (2S)-N-benzyl-2-bromo-3-hydroxypropanamide of Formula-XIX;

Yet another objective of the present invention is to prepare novel intermediate compound (2R)-2-azido-N-benzyl-3-hydroxypropanamide of Formula-XX.

SUMMARY OF THE INVENTION

Accordingly, the present invention provides a process to prepare (R)-N-Benzyl-2-acetamido-3-methoxypropanamide of Formula-I;

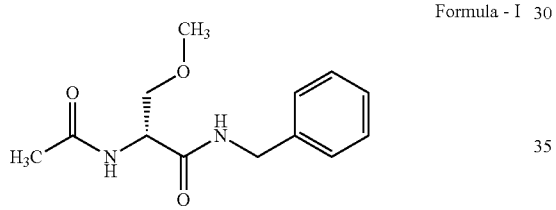

Formula - I comprising the steps of;
i. reacting (2S)-2-bromo-3-hydroxypropanoic acid of Formula-XVIII;

Formula - XVIII with benzylamine in presence of a base and an activator to get (2S)-N-benzyl-2-bromo-3-hydroxypropanamide of Formula-XIX;

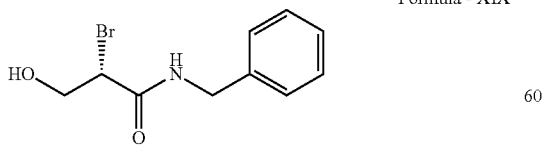

Formula - XIX ii. reacting the compound of Formula-XIX with sodium azide in presence of polar aprotic solvent to get (2R)-2-azido-N-benzyl-3-hydroxypropanamide of Formula-XX;

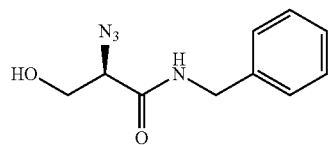

Formula - XX iii. hydrogenating the compound of Formula-XX using catalyst in presence of solvent to get the compound (2R)-2-amino-N-benzyl-3-hydroxypropanamide of Formula-II;

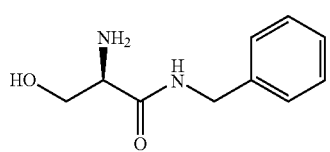

Formula - II iv. protecting the compound of Formula-II with di-tert-butyl dicarbonate to get the compound tert-butyl [(R)-2-(benzylamino)-1-(hydroxymethyl)-2-oxoethyl] carbamate of Formula-XXI;

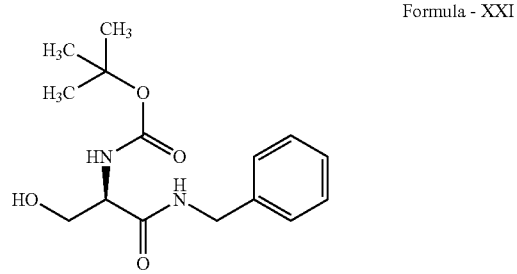 [SMILES: CC(C)(C)OC(=O)N[C@H](CO)C(=O)NCc1ccccc1]

Formula - XXI v. alkylating the hydroxyl group of the compound of Formula-XXI to isolate the compound (2R)-2-amino-N-benzyl-3-methoxypropanamide of Formula-VIII;

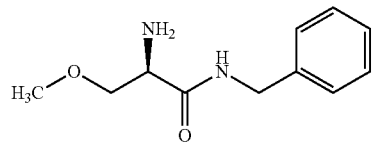

Formula - VIII vi. acetylating the compound of Formula-VIII in presence of a base and solvent to get (2R)-2-acetamido-N-benzyl-3-methoxypropanamide of Formula-I.

In an aspect, the process according to the present invention provides a novel intermediate compound (2S)-N-benzyl-2-bromo-3-hydroxypropanamide of Formula-XIX;

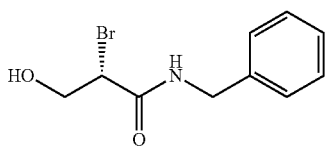

Formula - XIX

In another aspect, the process of the present invention discloses a novel intermediate compound (2R)-2-azido-N-benzyl-3-hydroxypropanamide of Formula-XX;

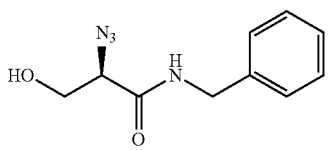

Formula - XX

DESCRIPTION OF THE INVENTION

The invention will now be described in detail in connection with certain preferred and optional embodiments, so that various aspects thereof may be more fully understood and appreciated.

The present invention provides an improved process to prepare the compound (2R)-2-acetamido-N-benzyl-3-methoxypropanamide of Formula-I. Further the present invention overcomes the inherent difficulties that exist in prior art when it is desirable to produce the product on commercial scale.

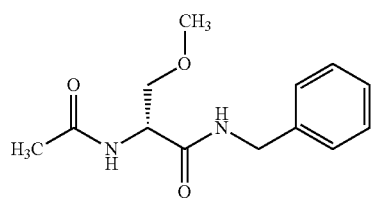

Formula - I

In one of the embodiments of the present invention, the compound (2S)-2-bromo-3-hydroxypropanoic acid of Formula-XVIII is subjected to react with benzylamine in presence of a base and an activator under mixed anhydride coupling condition to get (2S)-N-benzyl-2-bromo-3-hydroxypropanamide of Formula-XIX. The mixed anhydride coupling reaction conditions as described by Anderson, et al., in JACS, 1967, 89, 5012-5017, the contents of which are incorporated herein by reference. The activators used to activate the carbonyl group are selected from optionally substituted alkyl or aryl chloroformates such as methyl chloroformate, ethyl chloroformate, isobutyl chloroformate, phenyl chloroformate, pivolyl chloride, 1,1-carbonyldiimidazole, 1-ethyl-3-(3-dimethylaminopropyl)carbodiimide hydrochloride and N,N'-dicyclohexylcarbodiimide. The preferred activator used is alkyl chloroformate selected from methyl chloroformate, ethyl chloroformate and isobutyl chloroformate wherein the most preferred activator used is isobutyl chloroformate. The base used in the reaction is selected from N-methylmorpholine, pyridine, N,N-diisopropylethylamine and triethylamine wherein the preferred base used is N-methylmorpholine. The reaction is carried out in the presence of solvent at temperature in the range of −20° C. to 30° C. The solvent used for the reaction is selected from dichloromethane, ethyl acetate, toluene and tetrahydrofuran. The preferred solvent used for the reaction is ethyl acetate. Accordingly, the compound (2S)-2-bromo-3-hydroxypropanoic acid of Formula-XVIII is taken in ethyl acetate and the isobutyl chloroformate is charged at 20-30° C. Stirred and cooled the reaction mixture to −20° C. Maintaining the temperature at −20° C. charged base N-methylmorpholine and benzylamine to the reaction mass. The reaction is maintained between −20° C. to 30° C. for 4-10 hours. After completion of the reaction, concentrated the reaction mass under reduced pressure, maintaining temperature below 40° C. to get the residual mass. Charged non polar solvent to isolate the compound (2S)-N-benzyl-2-bromo-3-hydroxypropanamide of Formula-XIX. The non polar solvent used for isolation of the compound is selected from hexane, heptane and diisopropyl ether, wherein the preferred non polar solvent used is diisopropyl ether. Stirred and filtered the separated solid product, washed with water and dried to get the compound (2S)-N-benzyl-2-bromo-3-hydroxypropanamide of Formula-XIX.

The starting compound (2S)-2-bromo-3-hydroxypropanoic acid of Formula-XVIII used for the present invention is prepared as per the process disclosed in Organic Synthesis, Coll. Vol. 10, p. 401 (2004).

In another embodiment of the present invention, the benzyl aminated compound (2S)-N-benzyl-2-bromo-3-hydroxypropanamide of Formula-XIX is reacted with sodium azide in presence of polar aprotic solvent at a temperature in the range of 30-70° C. to get the compound (2R)-2-azido-N-benzyl-3-hydroxypropanamide of Formula-XX. The preferred temperature range for the reaction is 50-70° C. The polar aprotic solvent used for the reaction is selected from N,N-dimethylformamide, acetonitrile, N-methylpyrrolidone, dimethyl sulfoxide, and N,N-dimethylacetamide, wherein the preferred solvent used for the reaction is N,N-dimethylformamide. Accordingly, the compound (2S)-N-benzyl-2-bromo-3-hydroxypropanamide of Formula-XIX is taken in the solvent N,N-dimethylformamide and sodium azide is charged. Stirred and raised the reaction temperature up to 50° C. and maintained the reaction mass at 50-70° C. for 3 to 6 hours. The reaction is cooled and diluent ethyl acetate is added to the reaction mass. The pH of the reaction mass is adjusted to 9-9.5 with the help of dilute solution of base. The base used for the pH adjustment is selected from aqueous ammonia, sodium hydroxide, potassium hydroxide, sodium carbonate, sodium bicarbonate and potassium carbonate, wherein the preferred base used for the pH adjustment is sodium bicarbonate. The reaction is further diluted with water and separated the organic layer. Extracted the aqueous layer further with ethyl acetate and mixed with the organic layer. Concentrated the organic layer under reduced pressure below 40-45° C. to get the residual mass of azido compound (2R)-2-azido-N-benzyl-3-hydroxypropanamide of Formula-XX.

The advantage of the present invention is that, during the azido reaction the complete inversion of the stereo centre from (S) to (R) is achieved at 2 position of the benzylaminated compound. The compound disclosed herein can be enantiomerically pure and one enantiomer substantially free from other enantiomer can be prepared.

In another embodiment of the present invention, the compound (2R)-2-azido-N-benzyl-3-hydroxypropanamide of Formula-XX is hydrogenated in presence of polar solvent and catalyst to get the amino compound (2R)-2-amino-N-benzyl-3-hydroxypropanamide of Formula-II. The polar solvent used is selected from $C_1$-$C_4$ linear or branched alcohol and esters selected from methanol, ethanol, propanol, isopropyl alcohol, n-butanol, ethyl acetate, propyl acetate, isopropyl acetate, isoamyl acetate and butyl acetate. The preferred solvent used for hydrogenation is selected from ethyl acetate, propyl acetate, isopropyl acetate, isoamyl acetate and butyl acetate, wherein the most preferred solvent used for hydrogenation reaction is ethyl acetate. The catalyst used for the hydrogenation reaction is 5% palladium on carbon and 10% palladium on carbon. The amino compound (2R)-2-amino-N-benzyl-3-hydroxypropanamide of Formula-II, after the reaction is isolated from the reaction mass by filtration, concentration and purification using aliphatic acetate solvent selected from ethyl acetate, propyl acetate, isopropyl acetate, isoamyl acetate and butyl acetate either single or mixture thereof. The preferred solvent used for purification is ethyl acetate.

In another embodiment of the present invention, the benzylaminated compound (2S)-N-benzyl-2-bromo-3-hydroxypropanamide of Formula-XIX is reacted with sodium azide in presence of polar aprotic solvent at a temperature in the range of 30-70° C. The reaction mixture without isolating the intermediate is subjected to hydrogenation in presence of polar solvent and catalyst results in the compound (2R)-2-amino-N-benzyl-3-hydroxypropanamide of Formula-II. The preferred temperature range for the sodium azide reaction is 50-70° C. The polar aprotic solvent used for the reaction is selected from N,N-dimethylformamide, N-methylpyrrolidone, acetonitrile, dimethyl sulfoxide, and N,N-dimethylacetamide, wherein the preferred solvent used for the reaction is N,N-dimethylformamide. The catalyst used for the hydrogenation reaction is 5% palladium on carbon or 10% palladium on carbon. The polar solvent used is selected from $C_1$-$C_4$ aliphatic esters selected from ethyl acetate, propyl acetate, isopropyl acetate, isoamyl acetate and butyl acetate. The preferred solvent used for hydrogenation is ethyl acetate.

In yet another embodiment of the present invention the amino compound (2R)-2-amino-N-benzyl-3-hydroxypropanamide of Formula-II is reacted with di-tert-butyl dicarbonate in an organic solvent in presence of base at temperature in the range of 0° C.-40° C. to get the compound tert-butyl [(R)-2-(benzylamino)-1-(hydroxymethyl)-2-oxoethyl]carbamate of Formula-XXI. The solvent used for the reaction is selected from methanol, ethanol, propanol, isopropyl alcohol, n-butanol, ethyl acetate, propyl acetate, isopropyl acetate, isoamyl acetate and butyl acetate, dichloromethane and dichloroethane. The preferred solvent used for the reaction is selected from ethyl acetate, propyl acetate, isopropyl acetate, isoamyl acetate and butyl acetate, wherein the most preferred solvent used is ethyl acetate. The base used in the reaction is selected from triethylamine, pyridine, N-methylmorpholine, N-methylpyrrolidone, N-methylpiperidine and dimethylaminopyridine, wherein the preferred base used is triethylamine.

Accordingly the compound (2R)-2-amino-N-benzyl-3-hydroxypropanamide of Formula-II is charged in solvent and the base is added at 0° C. Maintaining the temperature at 0°-10° C. the compound di-tert-butyl dicarbonate is added and the reaction is continued at 0° C.-30° C. The reaction is carried out for 2-8 hours, concentrated under reduced pressure below 45° C. to get the residual mass of tert-butyl [(R)-2-(benzylamino)-1-(hydroxymethyl)-2-oxoethyl]carbamate of Formula-XXI. The residual mass tert-butyl [(R)-2-(benzylamino)-1-(hydroxymethyl)-2-oxoethyl]-carbamate of Formula-XXI obtained is isolated using non-polar solvent selected from hexane, heptane, cyclohexane, toluene and xylene, wherein the preferred solvent used for isolation of the compound is cyclohexane.

In another embodiment of the present invention, the O-alkylation of the compound tert-butyl [(R)-2-(benzylamino)-1-(hydroxymethyl)-2-oxoethyl]carbamate of Formula-XXI is performed by means of an alkylating agent in presence of base, a catalyst and an organic solvent. The alkylating agent used for the purpose of this invention is selected from dimethyl sulfate and trimethylsilyldiazomethane. The base used in the reaction is an aqueous solution of the base selected from metal hydrides, metal hydroxides and metal carbonates of sodium, potassium, lithium and calcium. The preferred base used is aqueous solution of sodium hydroxide. The organic solvent used for the reaction is selected form dichloromethane, dichloroethane, trichloroethane, tetrachloroethane, and toluene, wherein the preferred solvent used is dichloromethane. The catalyst used for the methylation reaction is a phase transfer catalyst selected from tetrabutylammonium bromide, tetrabutylammonium chloride, benzyltriethylammonium chloride and benzyltriethylammonium bromide. The preferred phase transfer catalyst used is tetrabutylammonium bromide. The methylation reaction is carried out at a temperature in the range of −15° C. to 15° C., wherein the preferred temperature range for the methylation reaction is −10° C. to 0° C.

Accordingly to a solution of the compound tert-butyl [(R)-2-(benzylamino)-1-(hydroxymethyl)-2-oxoethyl]carbamate of Formula-XXI in dichloromethane, charged the phase transfer catalyst and cooled the reaction mass to −10° C. and charged dilute solution of sodium hydroxide. Maintaining the temperature at −10° C.-0° C. charged dimethyl sulfate and maintained the reaction under stirring for 3-5 hours. Charged water at the end of the reaction, stirred, separated the organic layer and extracted the aqueous layer with the dichloromethane. Combined the organic layer and acidified with concentrated hydrochloric acid. Charged water to the clear solution and stirred. Separated the aqueous layer and extracted the organic layer further with water. Combined the entire aqueous layer and adjusted the pH to 12 with aqueous sodium hydroxide solution. Extracted the aqueous layer with dichloromethane and separated the organic layer. Extracted the aqueous layer further with dichloromethane to ensure the complete extraction of the desired product. The organic layer is washed and concentrated to isolate the compound (2R)-2-amino-N-benzyl-3-methoxypropanamide of Formula-VIII.

The compound of (2R)-2-amino-N-benzyl-3-methoxypropanamide of Formula-VIII is acetylated further using acetic anhydride in presence of base and solvent to isolate the crude compound (2R)-2-acetamido-N-benzyl-3-methoxypropanamide of Formula-I [Lacosamide]. The base used is selected from pyridine, N-methylmorpholine, triethylamine, N-methylpyrrolidine and N-methylpiperidine, wherein the preferred base used is triethylamine. The solvent used is selected from acetonitrile dichloromethane, ethyl acetate, cyclohexane and tetrahydrofuran or mixture thereof. The preferred solvent used for acetylation is ethyl acetate and cyclohexane either single or mixture thereof. The crude Lacosamide is further slurried in diethyl ether to isolate pure Lacosamide.

The reaction sequence of the present invention can be represented as given in scheme-5 below;

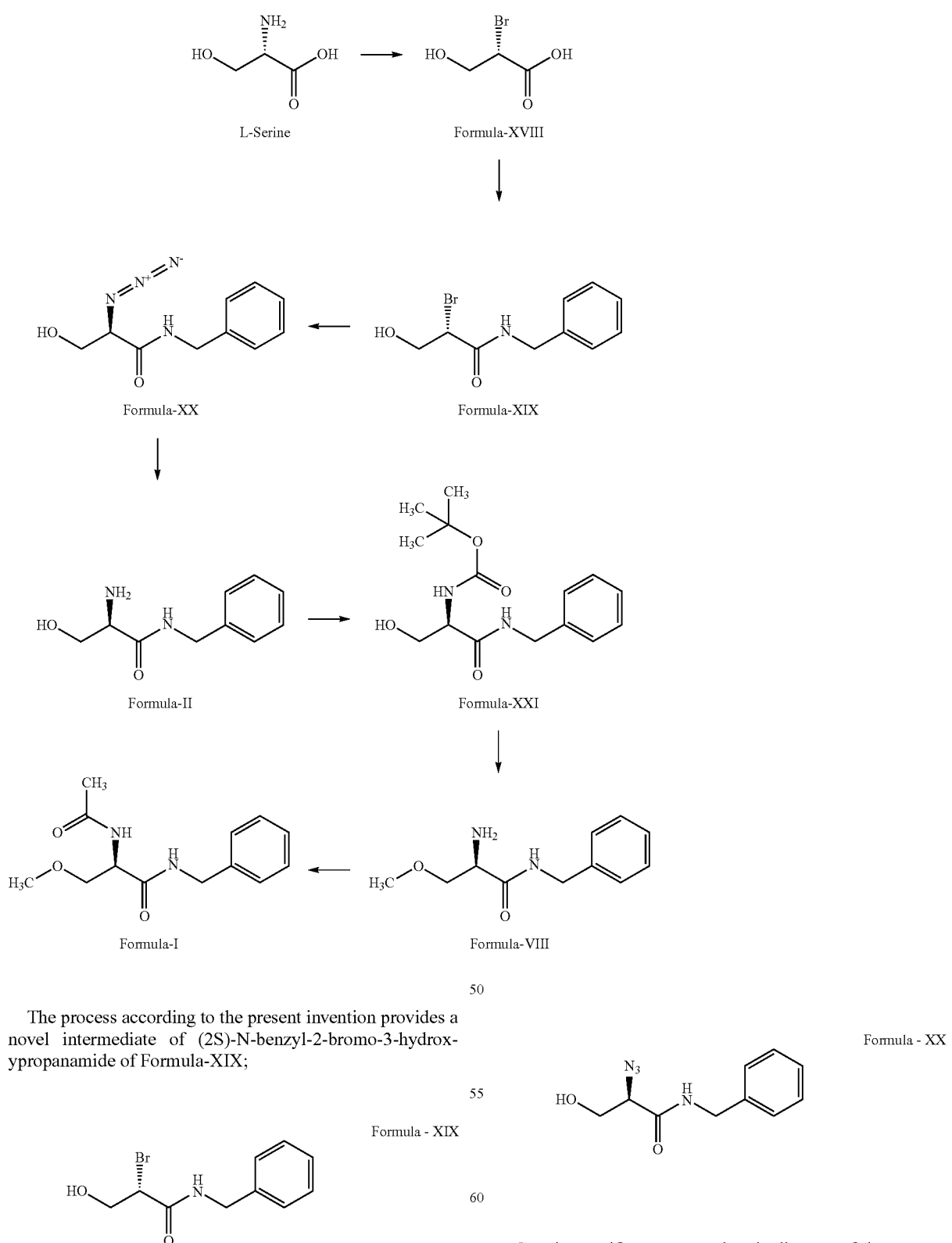

Scheme-5

The process according to the present invention provides a novel intermediate of (2S)-N-benzyl-2-bromo-3-hydroxypropanamide of Formula-XIX;

Formula - XIX

Also disclosed is a novel intermediate (2R)-2-azido-N-benzyl-3-hydroxypropanamide of Formula-XX which forms part of an embodiment.

Formula - XX

Certain specific aspects and embodiments of the present invention is further illustrated in detail with reference to the following examples, which are provided solely for the purpose of illustration and are not to be construed as limiting the scope of the invention in any manner.

EXAMPLES

Example-1

Preparation of (2S)-2-bromo-3-hydroxypropanoic acid.

To a solution of 100 g L-Serine and 385.23 g potassium bromide in 750 ml of water, aqueous solution of hydrobromic acid (47%, 238 ml) is added at 25-30° C. and the mixture is cooled under stirring to −15° C. to -12° C. Nitrogen is bubbled through the solution and slowly added, 80.87 g sodium nitrite in small lots within 2-2.5 hours. The solution is then allowed to warm to 0° C. and nitrogen purging is stopped. The reaction mixture is stirred for 3-4 hours at 0-10° C. Excess nitrogen oxides are removed by bubbling nitrogen through the solution for 1 hour. The aqueous layer is extracted with ethyl acetate (1×1000 ml, 2×500 ml). The combined organic extracts dried over anhydrous sodium sulphate and concentrated under reduced pressure at 35-40° C. to obtain pale yellow or green oil of (2S)-2-bromo-3-hydroxypropanoic acid.

Yield=138.0 gms.
% Yield=85.80%.

Example-2

Preparation of (2S)-N-benzyl-2-bromo-3-hydroxypropanamide.

To a solution of (2.9-2-bromo-3-hydroxypropanoic acid (138.0 g) in ethyl acetate (966.0 ml) isobutyl chloroformate (133.85 g) was added at 20-25° C. and cooled the reaction mass to −12° C. To this reaction mixture under nitrogen atmosphere the solution of N-methylmorpholine (107.23 g) and benzylamine (96.26 g) in ethyl acetate (178.0 ml) was added slowly maintaining temperature at −12° C. to −5° C. over a period of 1.0 hour. Maintained the reaction mixture at −5° to 0° C. for 30 minutes and raised the temperature slowly to 25-30° C. and maintained further for 1 hour. Reaction mass was concentrated under reduced pressure at 30° C. to 35° C. till one volume of the reaction mass remains in the reaction vessel. To the reaction mass was charged diisopropyl ether (300 ml) and distilled under reduced pressure till one volume of the reaction mass remains in the reaction vessel. To the reaction mass was charged diisopropyl ether (400 ml) and stirred the reaction mass for 30 minutes at 25-30° C. followed by addition of DM water (500 ml) and stirred for 30 minutes at 25-30° C. Filtered the solid separated and washed the cake with diisopropyl ether (2×100 ml) followed by DM water (500 ml) to get (2S)-N-benzyl-2-bromo-3-hydroxypropanamide. Dried the compound at 50-55° C. till constant weight.

Yield=140 g.
% Yield=66.40%.
$^1$H-NMR (400 MHz, DMSO-$d_6$) δ: 3.62 (1H, m), 3.83 (1H, m), 4.3 (3H, m), 5.42 (1H, $D_2O$ exchangeable), 7.27 (5H, m), 8.81 (1H, $D_2O$ exchangeable)
$^{13}$C-NMR (400 MHz, DMSO-$d_6$) δ: 42.799, 48.606, 63.113, 127.394, 127.624, 128.819, 139.310, 168.038
Mass: (M, M+2)=257.9 & 259.9 (1:1)

Example-3

Preparation of (2R)-2-azido-N-benzyl-3-hydroxypropanamide.

To a reaction flask was charged (2S)-N-benzyl-2-bromo-3-hydroxypropanamide (80.0 g) and sodium azide (30.23 g) in N,N-dimethylformamide (480 ml) and raised the temperature to 50-55° C. and maintained for 4-5 hours. Stopped heating and cooled the reaction mixture to 20-25° C. and charged DM water (400 ml), adjusted pH of the reaction mixture to 9-9.5 using 5% $NaHCO_3$ solution. Extracted the reaction mass with ethyl acetate (1×800 ml, 2×280 ml). Separated the organic layer and combined all ethyl acetate layers, washed with saturated ammonium chloride solution (2×240 ml). Concentrated the solvent ethyl acetate under reduced pressure to get oily compound of (2R)-2-azido-N-benzyl-3-hydroxypropanamide.

Yield=68.0 gms of oil.
% Yield=99.62%
$^1$H-NMR (400 MHz, $CDCl_3$) δ: 3.33 (1H, $D_2O$ exchangeable), 3.94-4.01 (2H, m), 4.12 (1H, t), 4.44 (2H, m), 6.93 (1H, s, $D_2O$ exchangeable), 7.25-7.36 (5H, m)
$^{13}$C-NMR (400 MHz, $CDCl_3$) δ: 43.62, 63.3, 64.67, 127.8, 127.88, 128.93, 137.32, 168.14
Mass: (M+)=221

Example-4

Preparation of (2R)-2-amino-N-benzyl-3-hydroxypropanamide.

In an autoclave charged (2R)-2-azido-N-benzyl-3-hydroxypropanamide (68.0 gms) in ethyl acetate (680 ml). Charged catalyst 5% Pd-C (6.85 gms) and closed the autoclave. Applied 3.8 kg Hydrogen pressure maintaining temperature at 25-30° C. and maintained the reaction mixture at 25-30° C. for 1.0 hour. After completion of the reaction, released Hydrogen pressure and flushed the autoclave with Nitrogen gas. Filtered the reaction mass through hyflo bed and washed hyflo bed with ethyl acetate. Concentrated filtrate under reduced pressure at 30-35° C. till two volumes of ethyl acetate remains in the reaction mixture. Removed vacuum and cooled the reaction mass to 0-5° C. and maintained for 2.0 hours. The reaction mass was filtered and washed with cold ethyl acetate (2×40 ml). Dried the product (2R)-2-amino-N-benzyl-3-hydroxypropanamide under vacuum at 25-30° C. till constant weight.

Yield=36.5 gms.
% Yield=60.86%.

Example-5

Preparation of (2R)-2-amino-N-benzyl-3-hydroxypropanamide.

To a reaction flask charged (2S)-N-benzyl-2-bromo-3-hydroxypropanamide (80.0 gms) and sodium azide (30.23 gms) in N,N-dimethylformamide (480 ml), stirred and raised the temperature to 50-55° C. and maintained for 4-5 hours. Stopped heating and cooled the reaction mixture to 20-25° C., charged DM water (400 ml), adjusted pH of the reaction mixture to 9-9.5 using 5% $NaHCO_3$ solution. Extracted the reaction mixture with ethyl acetate (1×800 ml, 2×280 ml) separated the organic layer and combined all ethyl acetate layers, washed with saturated ammonium chloride solution (2×240 ml). The ethyl acetate layer was taken for hydrogenation to 2 lit autoclave. Charged ethyl acetate layer and 5% Pd-C (6.85 gms) was added and closed the autoclave. Applied 3.8 kg Hydrogen pressure maintaining temperature at 25-30° C. and maintained the reaction mixture at 25-30° C. for 1.0 hour. After completion of the reaction released Hydrogen pressure and flushed the autoclave with Nitrogen gas. Filtered the reaction mass through hyflo bed and washed hyflo bed with ethyl acetate. Concentrated filtrate under reduced pressure at 30-35° C. till two volumes of ethyl acetate remains in the reaction mixture. Removed vacuum and cooled the reaction mass to 0-5° C. and maintained for 2.0 hours. The reaction mass was filtered and washed with cold ethyl acetate (2×40 ml). Dried the product (2R)-2-amino-N-benzyl-3-hydroxypropanamide under vacuum at 25-30° C. till constant weight.

Yield=36.5 gms.
% yield=60.63%.

Example-6

Preparation of tert-butyl [(1R)-2-(benzylamino)-1-(hydroxymethyl)-2-oxoethyl]carbamate.

To a solution of (2R)-2-amino-N-benzyl-3-hydroxypropanamide (34.0 gms) in ethyl acetate (170 ml), charged di-tert-butyl dicarbonate (45.89 gms) and stirred for 1.0 hour at 25-30° C. Charged triethylamine (1.77 gms) and stirred further for 1 hr at 25-30° C. After completion of reaction, concentrated the reaction mass under reduced pressure at 30-35° C. till 1 volume of ethyl acetate remained inside the reaction mass. Removed vacuum and charged cyclohexane (102 ml) and concentrated under reduced pressure till one volume of the solvent remained in the reaction mass. Charged cyclohexane (272 ml) and stirred at 25-30° C. for 1 hr. Filtered the reaction mass and washed with fresh cyclohexane. Dried the product Tert-butyl [(1R)-2-(benzylamino)-1-(hydroxymethyl)-2-oxoethyl] carbamate at 50-55° C. till constant weight.

Yield=47.2 gms
% Yield=91.65%

Example-7

Preparation of (2R)-2-amino-N-benzyl-3-methoxypropanamide.

In a reaction flask charged tert-butyl [(1R)-2-(benzylamino)-1-(hydroxymethyl)-2-oxoethyl]carbamate (110.0 gms) and tetrabutylammonium bromide (18.07 gms) in solvent dichloromethane (550 ml), stirred and cooled to −10° C. Charged aqueous solution of sodium hydroxide (75.0 gms in 195 ml of DM water) maintaining temperature at −10° C. to −5° C. Charged slowly within 1 hour, dimethyl sulfate (141.4 gms) maintaining temperature at −10° C. to −5° C. and maintained the reaction mass at −10° C. to −5° C. for 3.5 to 4.5 hrs. After completion of the reaction, charged DM water (550 ml) and stirred for 15 minutes at 25-30° C. Separated the organic layer and charged in the reaction flask. Charged conc. Hydrochloric acid (440 ml) within 15 min and maintained the reaction mixture at 25-30° C. for 1-2 hours. After completion of 2 hours charged DM water (330 ml) and stirred for 20-25 minutes. Separated the organic layer and washed with DM water (330 ml). Combined both aqueous layers and cooled to 15-20° C. to adjust pH of the solution to 13-14 with the help of 50% sodium hydroxide solution. Extracted the aqueous layer with dichloromethane (1×550 ml, 2×330 ml). Combined all dichloromethane layers and washed with DM water and stirred at 25-30° C. for 10-15minutes. Charcoalised dichloromethane layer at 25-30° C. for 30 minutes, filtered and washed the hyflow bed with dichloromethane (2×110 ml). Concentrated the filtrate under reduced pressure below 40° C. and degas under vacuum at 35-40° C. for 3-4hrs to get oily mass of (2R)-2-Amino-N-benzyl-3-methoxypropanamide.

Yield=70.6 gms
% Yield=90.71%.

Example-8

Preparation of (2R)-2-acetamido-N-benzyl-3-methoxypropanamide (Lacoasmide).

To a solution of (2R)-2-Amino-N-benzyl-3-methoxypropanamide (60.0 gms) and triethylamine (7.29 gms) in cyclohexane (600 ml) charged ethyl acetate (540 ml) and added acetic anhydride (35.29 gms) slowly maintaining the temperature at 25-30° C. in 15-20 minutes. Raised the temperature of the reaction mass to 35-40° C. and maintained for 4 hours. After completion of the reaction the reaction mass was cooled to 0 to 5° C. within 1 hour and maintained for 1.5 hours. Filtered the reaction mass at 0-5° C. and washed with cooled 1:1 mixture of ethyl acetate: cyclohexane (2×120 ml). The wet solid was taken in diethyl ether (612 ml) and stirred for 6 hours at 20-25° C. Filtered the product (2R)-2-acetamido-N-benzyl-3-methoxypropanamide and washed with diethyl ether and dried at 50-55° C. till constant weight.

Yield=53.48 gms,
% Yield=74.16%.

We claim:

1. A process for the preparation of (2R)-2-acetamido-N-benzyl-3-methoxypropanamide, comprising the steps of;
   a. reacting (2S)-2-bromo-3-hydroxypropanoic acid with benzylamine in the presence of a base and an activator to produce (2S)-N-benzyl-2-bromo-3-hydroxypropanamide;
   b. reacting (2S)-N-benzyl-2-bromo-3-hydroxypropanamide with sodium azide in a polar aprotic solvent to produce (2R)-2-azido-N-benzyl-3-hydroxypropanamide;
   c. hydrogenating (2R)-2-azido-N-benzyl-3-hydroxypropanamide to produce (2R)-2-amino-N-benzyl-3-hydroxypropanamide;
   d. alkylating the hydroxyl group of (2R)-2-amino-N-benzyl-3-hydroxypropanamide to produce (2R)-2-amino-N-benzyl-3-methoxypropan-amide; and
   e. acetylating the amino group of (2R)-2-amino-N-benzyl-3-methoxypropanamide to produce the compound (2R)-2-acetamido-N-benzyl-3-methoxypropanamide.

2. The process as claimed in claim 1, wherein said alkylating the hydroxyl group of step (d) comprises:
   i. protecting the amino group of (2R)-2-amino-N-benzyl-3-hydroxypropanamide; and
   ii. alkylating the hydroxyl group of the protected (2R)-2-amino-N-benzyl-3-hydroxypropanamide.

3. The process as claimed in claim 1, wherein said hydrogenation of step (c) comprises hydrogenating (2R)-2-azido-N-benzyl-3-hydroxypropanamide using a catalyst in the presence of a solvent.

4. The process as claimed in claim 2, wherein said protecting comprises protecting the amino group of (2R)-2-amino-N-benzyl-3-hydroxypropanamide with di-tert-butyl dicarbonate.

5. The process as claimed in claim 2, wherein said alkylating comprises alkylating the hydroxyl group of the protected (2R)-2-amino-N-benzyl-3-hydroxypropanamide in the presence of a catalyst.

6. The process as claimed in claim 1, wherein said acetylation of step (e) comprises acetylating the amino group of (2R)-2-amino-N-benzyl-3-methoxypropanamide in the presence of a base and a solvent.

7. The process as claimed in claim 1, wherein the activator used for the reaction in step (a) is selected from the group consisting of methyl chloroformate, ethyl chloroformate, isobutyl chloroformate, phenyl chloroformate, pivolyl chloride, 1,1-carbonyl diimidazole, 1-ethyl-3-(3-dimethylaminopropyl)carbodiimide hydrochloride and N,N'-dicyclohexylcarbodiimide.

8. The process as claimed in claim 7, wherein the activator used for the reaction in step (a) is isobutyl chloroformate.

9. The process as claimed in claim 1, wherein the base used for the reaction in step (a) is selected from the group consisting of triethylamine, N-methylmorpholine, pyridine and N,N-diisopropylethylamine.

10. The process as claimed in claim 8, wherein the base used for the reaction in step (a) is N-methylmorpholine.

11. The process as claimed in claim 1, wherein the reaction of step (a) is carried out at temperature of between about −20° C. and about 30° C., in the presence of a solvent selected from the group consisting of dichloromethane, ethyl acetate, toluene and tetrahydrofuran.

12. The process as claimed in claim 1, wherein the polar aprotic solvent used in step (b) is selected from the group consisting of N,N-dimethylformamide, N-methylpyrrolidone, dimethyl sulfoxide, acetonitrile and N, N-dimethylacetamide.

13. The process as claimed in claim 3, wherein said hydrogenation comprises hydrogenating (2R)-2-azido-N-benzyl-3-hydroxypropanamide using a catalyst comprising palladium on carbon.

14. The process as claimed in claim 3, wherein said hydrogenation is carried out in presence of a solvent selected from the group consisting of methanol, ethanol, propanol, isopropyl alcohol, n-butanol, ethyl acetate, propyl acetate, isopropyl acetate, isoamyl acetate and butyl acetate.

15. The process as claimed in claim 5, wherein said alkylating comprises alkylating the hydroxyl group of the protected (2R)-2-amino-N-benzyl-3-hydroxypropanamide with an alkylating agent selected from the group consisting of dimethyl sulfate and trimethylsilyldiazomethane.

16. The process as claimed in claim 1, wherein said alkylation of step (d) is performed in the presence of a base and a solvent, at temperature between about −15° C. and about 15° C.

17. The process as claimed in claim 5, wherein said alkylating is performed in the presence of a phase transfer catalyst selected from the group consisting of tetrabutylammonium bromide, tetrabutylammonium chloride, benzyltriethyl-ammonium chloride and benzyltriethylammonium bromide.

18. The process as claimed in claim 6, wherein said acetylating comprises acetylating the amino group of (2R)-2-amino-N-benzyl-3-methoxypropanamide in the presence of a base and a solvent selected from the group consisting of acetonitrile, dichloromethane, ethyl acetate, cyclohexane, tetrahydrofuran and a mixture thereof.

19. The process as claimed in claim 17, wherein said acetylating comprises acetylating the amino group of (2R)-2-amino-N-benzyl-3-methoxypropanamide in the presence of a base and a solvent selected from the group consisting of ethyl acetate, cyclohexane, and a mixture thereof.

20. The compound (2S)-N-benzyl-2-bromo-3-hydroxypropanamide of Formula-XIX:

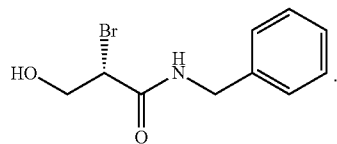

Formula - XIX

21. The compound (2R)-2-azido-N-benzyl-3-hydroxypropanamide of Formula-XX:

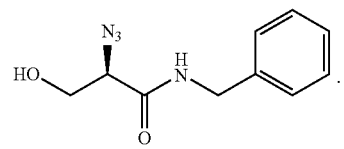

Formula - XX

* * * * *